United States Patent
Starke et al.

(10) Patent No.: US 9,306,307 B2
(45) Date of Patent: Apr. 5, 2016

(54) CONTACT ELEMENT AND METHOD FOR PRODUCING A CONTACT ELEMENT

(71) Applicant: BIOTRONIK SE & Co. KG, Berlin (DE)

(72) Inventors: Marcel Starke, Eichwalde (DE); Ronald Rebentisch, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 14/584,350

(22) Filed: Dec. 29, 2014

(65) Prior Publication Data

US 2015/0214650 A1    Jul. 30, 2015

Related U.S. Application Data

(60) Provisional application No. 61/932,819, filed on Jan. 29, 2014.

(51) Int. Cl.
*H01R 13/33* (2006.01)
*H01R 13/24* (2006.01)
*H01R 43/28* (2006.01)
(Continued)

(52) U.S. Cl.
CPC .......... *H01R 13/2421* (2013.01); *A61N 1/3752* (2013.01); *B21F 11/005* (2013.01); *H01R 13/187* (2013.01); *H01R 13/33* (2013.01); *H01R 43/28* (2013.01); *H01R 24/58* (2013.01);
(Continued)

(58) Field of Classification Search
CPC ............... H01R 13/2421; H01R 13/33; H01R 2201/12; A61N 1/3752

USPC .............. 439/841, 840, 786, 909, 733.1; 200/276; 607/37
See application file for complete search history.

(56) References Cited

U.S. PATENT DOCUMENTS 6,895,276 B2 *   5/2005   Kast ................... A61N 1/3752
                                                      439/909
7,110,827 B2 *   9/2006   Sage .................. A61N 1/3752
                                                      439/909
(Continued)

FOREIGN PATENT DOCUMENTS

DE           690 27 846       11/1996
DE     10 2004 002 404 B3      9/2005
(Continued)

OTHER PUBLICATIONS

European Search Report and Notes to the European Search Report on European Patent Application No. EP 15 15 0319, dated Jun. 15, 2015 (9 pages).

*Primary Examiner* — Abdullah Riyami
*Assistant Examiner* — Harshad Patel
(74) *Attorney, Agent, or Firm* — Buchanan Ingersoll & Rooney PC

(57) ABSTRACT

An electrical contact element, in particular for a medical implant, including a spring sleeve with a bushing for receiving an electrical mating contact in a direction of insertion, at least one groove that is arranged transversely around the bushing at least in areas and that is open to the bushing at least in areas; at least one spring element, arranged in the groove, for electrically contacting the electrical mating contact. Here, at least one feed-through channel is provided to feed the spring element into the peripheral groove and leads from an outer face of the spring sleeve to the at least one groove. The invention further relates to a method for producing a contact element and also to a device for carrying out the method.

13 Claims, 6 Drawing Sheets

(51) Int. Cl.
*B21F 11/00* (2006.01)
*A61N 1/375* (2006.01)
*H01R 13/187* (2006.01)
*H01R 24/58* (2011.01)

(52) U.S. Cl.
CPC ....... *H01R2201/12* (2013.01); *Y10T 29/49204* (2015.01); *Y10T 29/53274* (2015.01)

(56) References Cited

U.S. PATENT DOCUMENTS

| | | | | |
|---|---|---|---|---|
| 7,914,351 B2 * | 3/2011 | Balsells | ............... | H01R 11/286 439/840 |
| 8,753,153 B2 * | 6/2014 | Leon | ................... | B21F 1/00 439/840 |
| 2004/0034393 A1 * | 2/2004 | Hansen | ................ | A61N 1/3752 607/37 |
| 2005/0027325 A1 * | 2/2005 | Lahti | .................... | A61N 1/3752 607/37 |
| 2006/0047322 A1 * | 3/2006 | Naviaux | ............... | A61N 1/3752 607/37 |
| 2008/0255631 A1 * | 10/2008 | Sjostedt | ............ | A61N 1/3752 607/37 |
| 2010/0197174 A1 * | 8/2010 | Lahti | .................... | A61N 1/3752 439/733.1 |
| 2010/0233896 A1 * | 9/2010 | Dilmaghanian | ..... | A61N 1/3752 439/271 |
| 2012/0003880 A1 * | 1/2012 | Glick | .................... | H01R 13/187 439/786 |
| 2012/0129409 A1 * | 5/2012 | Drew | .................. | A61N 1/3752 439/843 |

FOREIGN PATENT DOCUMENTS

| | | |
|---|---|---|
| DE | 20 2013 104131 U1 | 9/2013 |
| GB | 774419 | 5/1957 |
| WO | 89/05170 | 6/1989 |

* cited by examiner

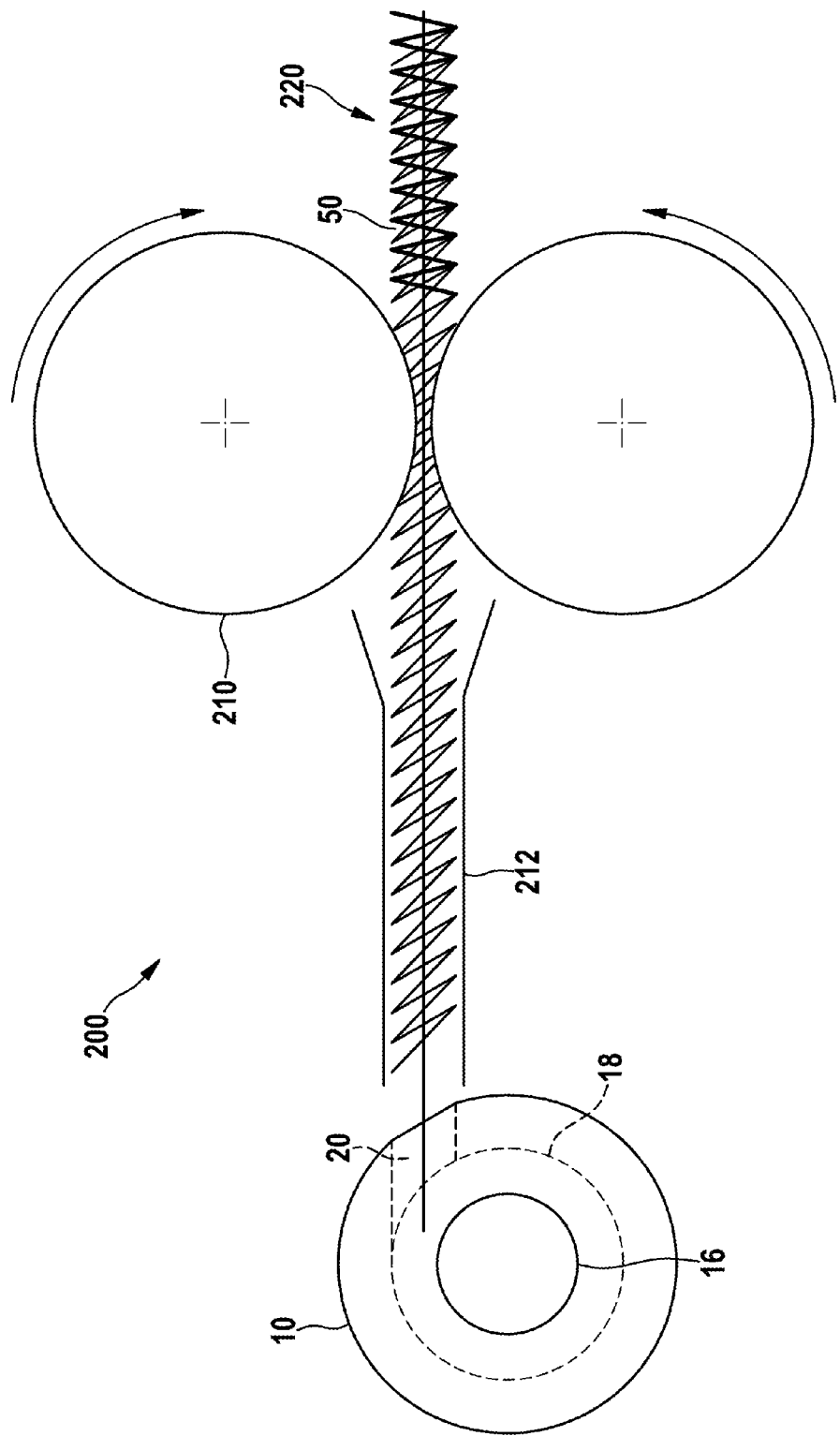

CONTACT ELEMENT AND METHOD FOR PRODUCING A CONTACT ELEMENT

CROSS-REFERENCE TO RELATED APPLICATIONS

This patent application claims the benefit of co-pending U.S. Provisional Patent Application No. 61/932,819, filed on Jan. 29, 2014, which is hereby incorporated by reference in its entirety.

TECHNICAL FIELD

The present invention relates to an electrical contact element and to a method for producing an electrical contact element according to the preambles of the independent claims.

BACKGROUND

Medical implants which can be inserted into the human or animal body and which require an electrical supply voltage need a particularly reliable and lasting electrical contacting. Such implants include, for example, cardiac pacemakers, defibrillators, neurostimulators, and the like.

An electrical contact element for medical implants that can be inserted into the human or animal body is known from German Patent No. DE 690 27 846, in which an electrical connection is produced via a torus spring and a pin of a plug contact. The torus spring is inserted into a groove in a bushing, wherein the electrical contact is formed between the pin and the inner circumference of the torus spring.

The fabrication of torus springs, in particular closed torus springs, and the assembly thereof by insertion into the peripheral groove of corresponding spring sleeves is complex and can only be automated with difficulty and, as a result, is accordingly costly.

The present invention is directed toward overcoming one or more of the above-mentioned problems.

SUMMARY

An object of the present invention is to create an electrical contact element that can be produced at least largely in an automated manner.

Further objects of the present invention are to specify an automated method for producing such a contact element and also a device for carrying out the method.

At least these objects are achieved in accordance with the present invention by the features of the independent claims. Favorable embodiments and advantages of the present invention will emerge from the further claims and from the description.

In accordance with a first aspect of the present invention, an electrical contact element is proposed, in particular, for a medical implant for insertion into the human or animal body, comprising:

at least one spring sleeve with a bushing for receiving an electrical mating contact in a direction of insertion;

at least one groove that is arranged around the bushing, at least transversely around the bushing, and that is open to the bushing at least in areas; and at least one spring element, which is arranged in the groove, for electrically contacting the electrical mating contact;

wherein at least one feed-through channel for feeding the spring element into the at least one groove is provided and leads from an outer face of the spring sleeve to the at least one groove.

The inserted spring element, at least at the areas open to the bushing, may form an electrical contact surface for a mating contact inserted into the bushing, said electrical contact surface bearing resiliently against the mating contact. The groove is expediently arranged at a constant axial height with respect to the longitudinal axis of the bushing. It is also conceivable, however, for the groove to have a gradient. The groove may be formed so as to run around the bushing or may also be divided into individual groove portions. These can be interconnected or separate from one another. The groove may have one or more feed-through channels. One or more feed-through channels may also be provided for each groove portion.

The feed-through channel may advantageously be arranged tangentially to the groove. The spring element can thus be guided particularly easily, in particular, if the groove and the bushing are arranged in a manner running around the bushing. Alternatively, the feed-through channel may approach the groove radially. Intermediate stages of the orientation of the feed-through channel relative to the groove between the tangential and radial approach toward the groove are also conceivable. It is also conceivable, in the case of a plurality of feed-through channels for the same groove or respective groove portions for an associated electrical contact area, for the feed-through channels to have identical or different orientations relative to the groove or groove portions.

In an embodiment, the free end of the spring element may be led out through a second radial feed-through channel at any point on the circumference of the spring sleeve in order to produce a spring contact that runs around only in part. In the case of the use of just one spring element, this may also be a torus spring element that is not completely closed and that, for example, can be introduced through a first feed-through channel and led out again from the groove in an additional further feed-through channel running tangentially to the groove. This second feed-through channel may be guided, for example, approximately parallel to the first feed-through channel. Further embodiments provide two or more spring elements, such that these are substantially elongate, but may also have a slight curvature. The channels for inserting and leading out the spring element may be arranged here in a largely aligned manner or slightly offset. For example, three elongate spring elements, which each enclose 120° between adjacent spring elements, are also conceivable.

The spring element may advantageously be fed automatically and possibly canted beforehand. Manual insertion of a ready-made torus spring into the peripheral groove is not necessary. The spring element may favorably be an open wire coil not closed in an annular manner. For example, the spring element may be formed from platinum-iridium.

A contact device may have, for example, a plurality of contact elements of this type with spring sleeves arranged sequentially in an axial direction, wherein the peripheral grooves are arranged parallel to one another, such that a mating of contact with contact areas electrically insulated from one another can come into contact with the respective spring elements of the respective spring sleeves.

Due to the specific design of the spring sleeve with feed-through channel approaching the peripheral groove tangentially, a wire coil wound in a continuous method can be fed fully and automatically as a canted, tailor-cut spring element and can be connected via one end to the spring sleeve by means of a joining technique.

In a favorable embodiment, the spring element can be fixedly connected at least at one point to the spring sleeve. The spring element may advantageously be welded to the spring sleeve at a point, for example, in the area of the feed-through channel. In particular, the spring element can be laser-welded to the spring sleeve, which allows a particularly accurate placing of the weld point.

In a further favorable embodiment, the spring element can be inserted into the peripheral groove of the spring sleeve so far that a leading free end of the spring element contacts a trailing area of the spring element. A large contact area for an electrical mating contact, for example, a pin, can therefore be provided. The spring element may favorably be an open wire coil not closed in an annular manner.

In a further favorable embodiment, the spring element may protrude from the tangential feed-through channel. The protruding end of the spring element can be used to electrically contact the spring sleeve itself. Alternatively, the spring element may finish flush with the feed-through channel, and the spring sleeve may be electrically contacted at a different point.

The spring sleeve may particularly preferably be formed in two or more parts, wherein the groove may be arranged in the parting plane. In this embodiment, it is particularly preferable for the groove to have an undercut when the two spring sleeve parts are joined together, such that, in the assembled state of the multi-part spring sleeve, the spring element is enclosed over more than half of its circumference by the groove.

The spring element may advantageously be a wire coil. The wire coil may thus be produced similarly to coils for cardiac pacemaker electrode feed lines, that is to say such a coil may be wound from a wire or a plurality of individual wires and can be prefabricated in larger length units. This allows a particularly cost-effective production of the spring element.

In accordance with a further aspect of the present invention, a method for producing a contact element according to the present invention is proposed, wherein a wire coil is transported via a guide element into a spring sleeve having a radial feed-through channel and is inserted as a spring element through the radial feed-through channel into a groove and is shortened to a desired length. This allows a cost-effective production of a contact element.

In accordance with a favorable method step, the wire coil can be inserted so far into the groove until a leading free end of the spring element contacts a trailing area of the spring element. A maximum electrical contact area can therefore be provided. Alternatively, the leading free end of the wire coil can be led out through a second radial exit channel, wherein the position of the exit channel can be selected arbitrarily. This exit channel runs in an opposed tangential direction relative to the peripheral groove. With the aid of this radial exit channel, it is possible to produce a spring element that runs around only in part.

In accordance with a favorable method step, the wire coil can be transported from a winding process via a canting stage to the guide element.

In this case, the wire coil can be produced similarly to coils for cardiac pacemaker electrode feed lines, that is to say this coil can be wound from a plurality of individual wires and can be prefabricated in larger length units. Portions can be separated from these larger length units, for example, by means of a laser-cutting method, said portions being so long that they (introduced through the tangential feed-through channel) completely fill the groove that runs around and at the other end still protrude slightly from the feed-through channel.

Once inserted into the spring sleeve, the protruding end of the wire coil or of the spring element can be fixed in this position by means of, for example, a laser weld point.

In accordance with a further aspect of the present invention, a device for carrying out the method according to the present invention is proposed, comprising a transport mechanism in order to transport a wire coil via a guide element to a spring sleeve and to insert said wire coil through a radial feed-through channel into a groove in the spring sleeve, and further comprising a cutting mechanism in order to separate a spring element from the wire coil and to cut said spring element to a desired length, and also comprising a connection unit in order to fixedly connect the spring element to the spring sleeve at least at one point.

A canting stage may advantageously be provided in order to cant the wire coil before the insertion into the groove.

Cost savings are advantageously possible by a production process that has a high potential for automation. The wire coil can be transported directly from the winding process via the canting stage, for example, formed of two rotating rolls, and may travel via a guide element into the spring sleeve with radial feed-through channel.

The inserted spring element can be used as a wiring element and can be welded automatically at a point to the spring sleeve and separated in a suitable length. Alternatively, the spring element can be welded flush to the spring sleeve and cut to length.

Further features, aspects, objects, advantages, and possible applications of the present invention will become apparent from a study of the exemplary embodiments and examples described below, in combination with the Figures, and the appended claims.

DESCRIPTION OF THE DRAWINGS

The present invention is described in greater detail hereinafter by way of example on the basis of exemplary embodiments illustrated in drawings, in which;

FIG. 12 shows a schematic view of an advantageous embodiment of a device for producing a contact element.

DETAILED DESCRIPTION

In the Figures, functionally like elements or elements acting in the same way are denoted by the same reference signs. The Figures are schematic illustrations of exemplary embodiments of the present invention. They do not show specific parameters of the present invention. Furthermore, the Figures merely reproduce typical exemplary embodiments of the present invention and are not intended to limit the present invention to the illustrated embodiments.

Figure 1:
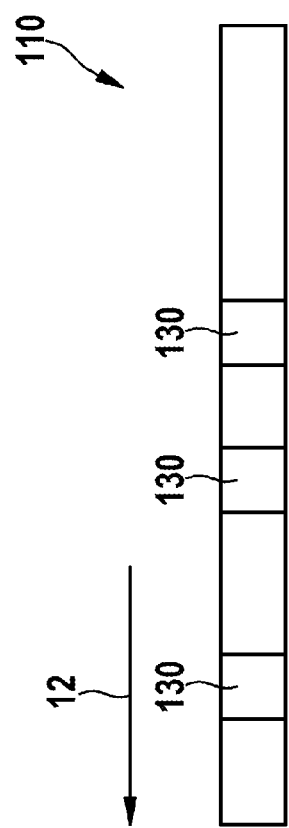
FIG. 1 shows a schematic illustration of a contact device having contact elements in accordance with a first embodiment of the present invention.
Figure 1:
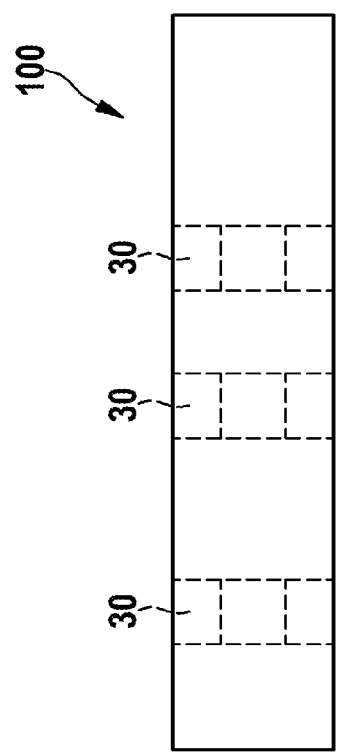

FIG. 1 shows a schematic view of an embodiment of a contact device 100 having a plurality of electrical contact elements 30, for example three electrical contact elements. More or less electrical contacts are contemplated. Details concerning a medical implant to which the contact device 100 and an electrical mating contact 110 associated therewith are coupled, such as, for example, attached components, electrical component parts and the like, are not illustrated, as these details are readily understood by one skilled in the art.

The electrical mating contact 110, for example, a pin, is to be inserted in the direction 12 of a longitudinal axis into the contact device 100. Here, the electrical mating contact 110 is led through the contact elements 30. The electrical mating contact 110 has on its outer face a plurality of contact areas 130, for example, three contact areas, which come into contact with the contact elements 30 when the electrical mating contact 110 is inserted into the contact device 100. Again, more or less contact areas are contemplated.

Figure 2:
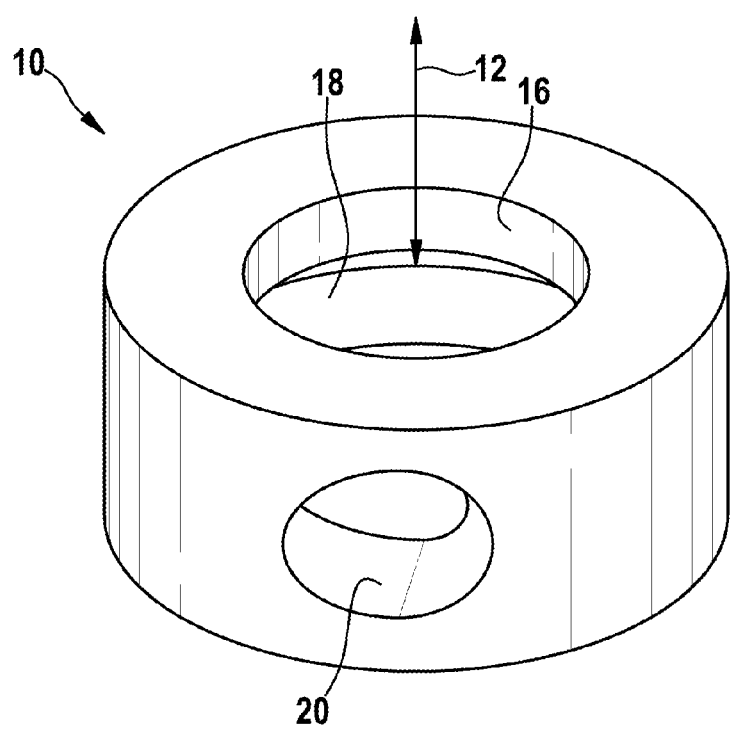
FIG. 2 shows a schematic view of a first embodiment of a spring sleeve with a lateral bore as a feed-through channel approaching a groove in the spring sleeve tangentially.
Figure 3:
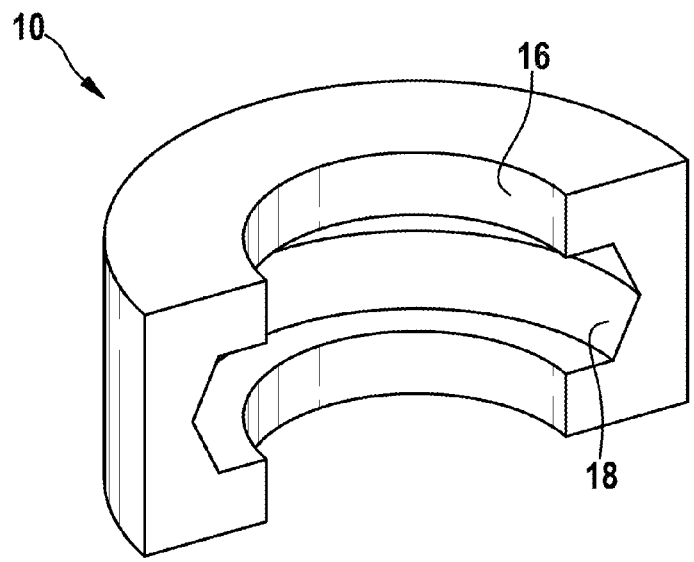
FIG. 3 shows a schematic sectional view of the spring sleeve from FIG. 2.
Figure 4:
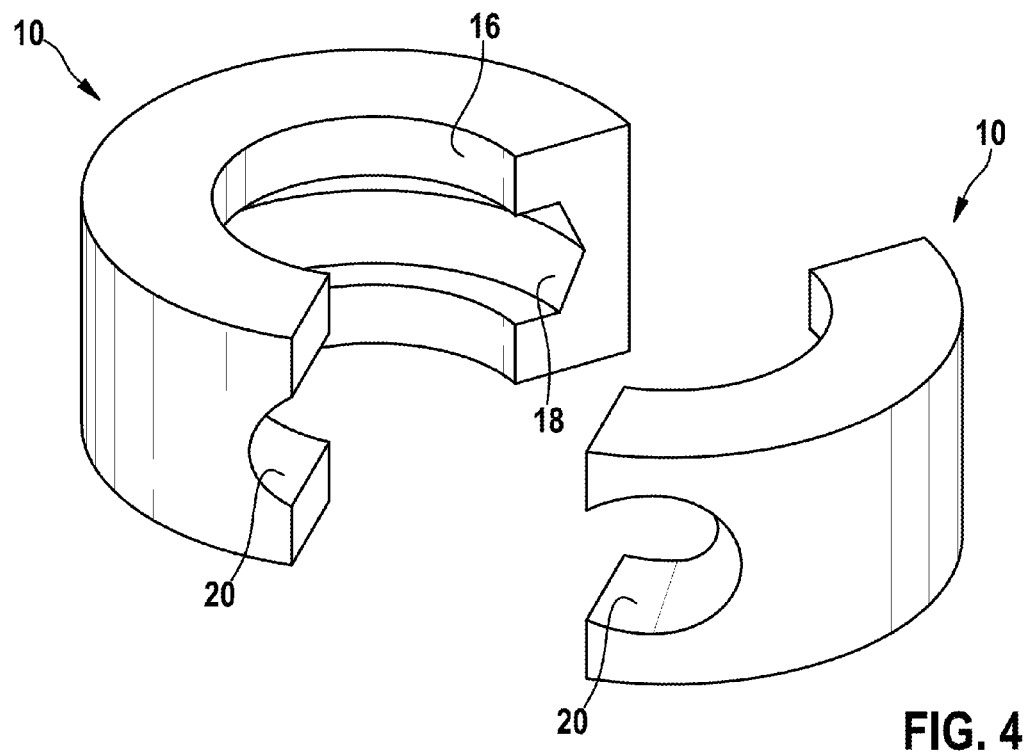
FIG. 4 shows a schematic view of two separate pieces of the spring sleeve from FIG. 2.

FIGS. 2, 3 and 4, for the purpose of explaining the present invention, show various views and sections of a first embodiment of an electrical contact element 30, in particular, for a medical implant, comprising a spring sleeve 10 with a bushing 16 for receiving an electrical mating contact (not illustrated) in a direction of insertion 12.

A groove 18 that runs around the bushing 16 and is open toward the bushing 16 is arranged around the bushing 16 extending in the axial direction 12 and lies in a plane transverse to the direction 12. The groove 18 is intended to receive a spring element 52 (see FIG. 7) and to electrically contact the electrical mating contact (not illustrated).

A bore is arranged tangentially to the peripheral groove 18 in the spring sleeve 10 and acts as a feed-through channel 20 for feeding the spring element 52 into the peripheral groove 18. The feed-through channel 20 approaches the groove 18 from the outer face of the spring sleeve 10 and is arranged in the same plane as the groove 18. The groove 18 may have a prismatic (angular) profile, for example.

In the embodiment illustrated here, the spring sleeve 10 is formed in two parts. The spring sleeve is separated in the plane that is transverse to the direction 12 and runs precisely over the centerline of the peripheral groove 18 that is created when the two spring sleeve parts are assembled. In other words, the groove 18 lies in the parting plane, in which the spring sleeve 10 is separated, and is completed by the assembly process. Specifically, both parts of the spring sleeve 10 are each provided with a complementary portion of the groove 18. The specific feature of the spring sleeve 10 divided into two parts, as illustrated here, is that in the joined state of the two spring sleeve parts, a groove 18 is created for the spring element 52 by two undercuts. In the assembled state, the spring element 52 is therefore enclosed over more than half its circumference by the groove 18. The spring element 52 is therefore prevented from slipping from the groove upon actuation of the spring sleeve 10, which is of considerable significance in the case of an open spring element 52. These two-part spring sleeves 10 can be produced cost-effectively, for example, and therefore particularly economically by means of forming methods, such as, for example, injection molding or casting.

The spring sleeve 10 is cylindrical, for example. The contact element may also comprise a plurality of spring sleeves 10 of this type, which are arranged concentrically with the axis of symmetry and sequentially in the direction 12 (not illustrated).

Figure 5:
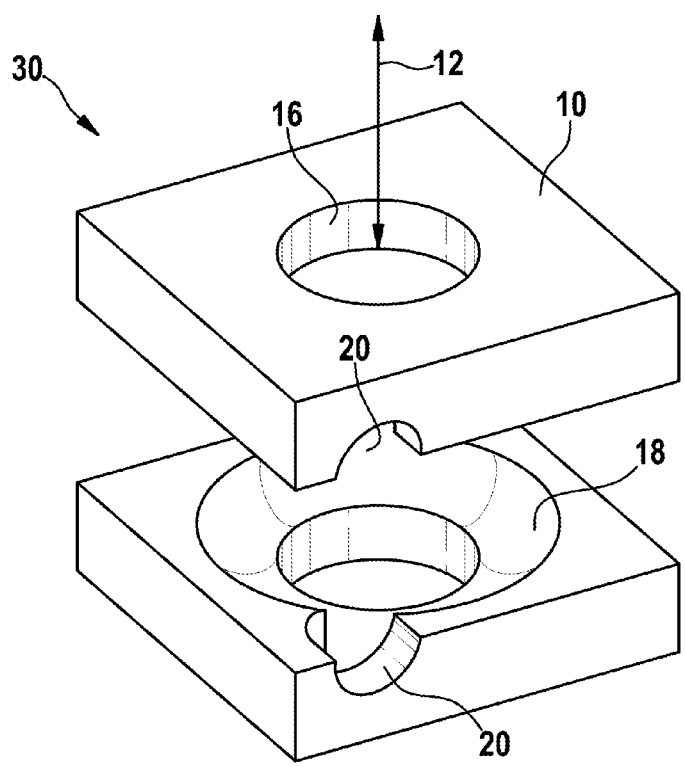
FIG. 5 shows a schematic view of a further embodiment of a spring sleeve with a bore in the end face as a feed-through channel approaching a groove in the spring sleeve tangentially, illustrated in two separate pieces.
Figure 6:
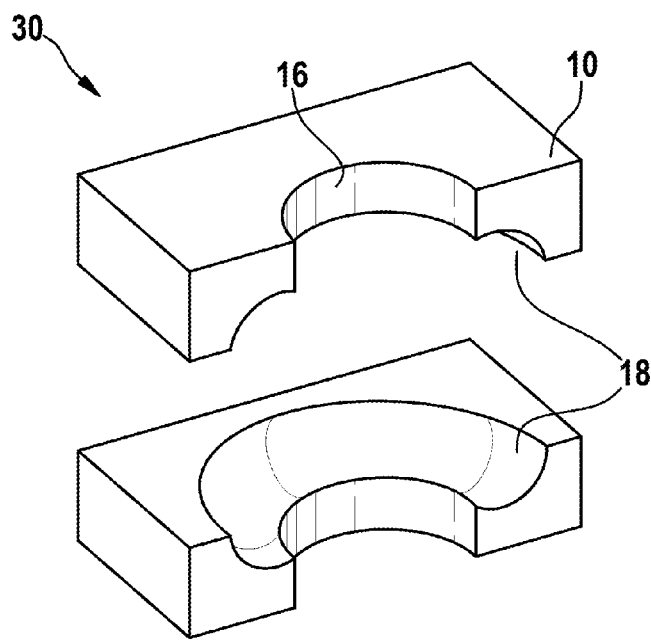
FIG. 6 shows a schematic sectional view through the separate pieces of the spring sleeve from FIG. 5.

FIGS. 5 and 6 show a further embodiment of a contact element 30, in which the spring sleeve 10 has a rectangular, in particular, square, cross section. The groove 18 may have a rounded profile, for example. The feed-through channel 20 is formed as a bore in an end face of the spring sleeve 10, said bore approaching the groove 18 in the interior of the spring sleeve 10 tangentially.

Figure 7:
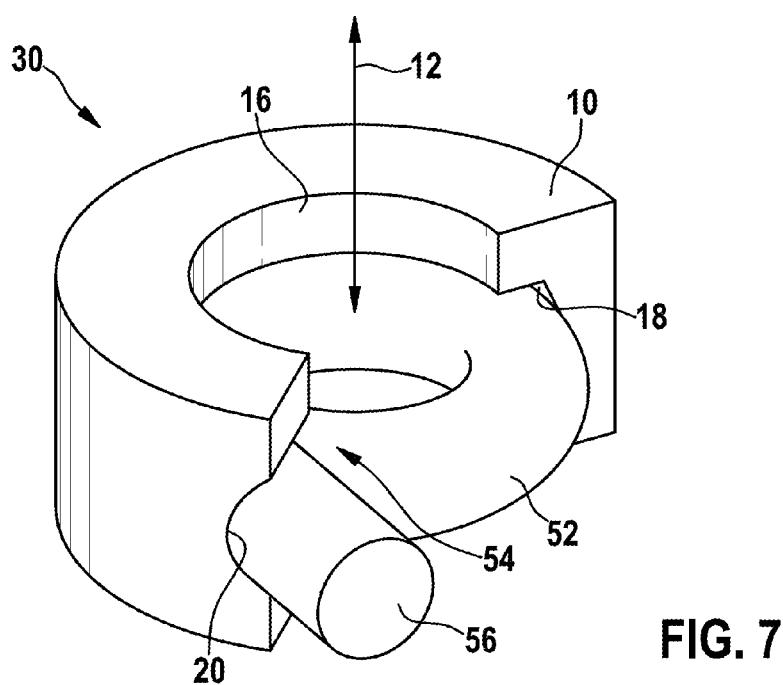
FIG. 7 shows a schematic view of a partly cut spring sleeve with a spring element inserted into a groove.

FIG. 7 shows a partly cut spring sleeve 10 with a spring element 52 inserted into a groove 18. The groove 18 is arranged in a manner running around a bushing 16 concentrically. If an electrical mating contact, for example, a pin (not illustrated), is inserted into the bushing 16 in the direction 12, it comes into contact with the spring element 52 and produces an electrical connection between the spring element 52 and the mating contact. The spring element 52 is fixedly connected, for example, welded, to the spring sleeve 10 at least at one point in order to be fixed in position.

The spring element 52 is inserted so far into the peripheral groove 18 in the spring sleeve 10 that a leading free end 54 of the spring element 52 contacts a trailing area of the spring element 52.

In the shown embodiment, the spring element 52 protrudes, at 56, from the tangential feed-through channel 20 and can be used as a connection point for an electrical contacting of the spring sleeve 10. Alternatively, the spring element 52 may finish flush with the feed-through channel 20 (not illustrated).

Figure 8:
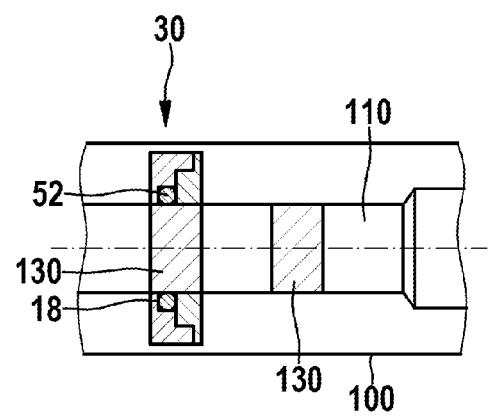
FIG. 8 shows a schematic view of an electrical contact area of a mating contact in contact with a spring sleeve.

FIG. 8 shows a schematic view of an electrical contact area 130 of a mating contact 110 in contact with a spring sleeve 30 cut transversely. The spring sleeve 30 may advantageously be composed from disk-like sub-elements, wherein a groove 18 for the spring element 52 is formed in the assembled state.

Figure 9:
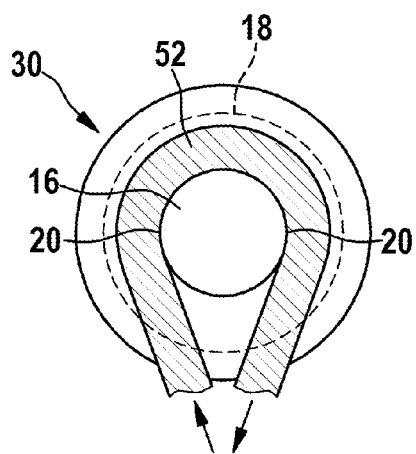
FIG. 9 shows a schematic view of a favorable embodiment of a spring sleeve with spring element.
Figure 10:
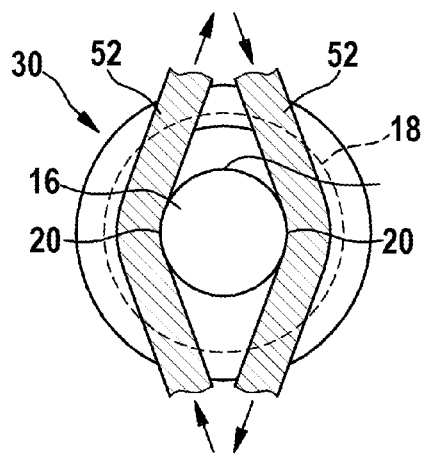
FIG. 10 shows a schematic view of a favorable embodiment of a spring sleeve with two spring elements.
Figure 11:
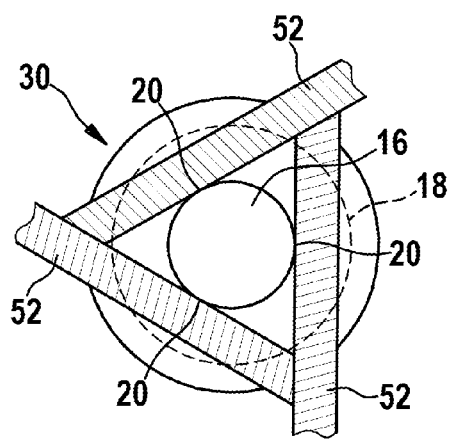
FIG. 11 shows a schematic view of a favorable embodiment of a spring sleeve with three spring elements.

FIGS. 9, 10 and 11 illustrate exemplary favorable embodiments of a spring sleeve 30 having a plurality of channels 20, which serve to lead through a spring element 30. FIG. 9 shows two feed-through channels 20 arranged side by side. A spring element 52 is inserted through one of the feed-through channels 20 and may exit with its free end through the adjacent feed-through channel 20. The spring element 52 can be cut to length accordingly and possibly fixed to the spring sleeve 30, as has already been described above. The spring element 52 surrounds the bushing 16 to a large extent here.

FIG. 10 shows a favorable embodiment of a spring sleeve 30 with two spring elements 52, each of which is inserted on one side of the spring sleeve 30 through an separate insertion channel 20 into the spring sleeve 30, and on the opposite side of the spring sleeve may protrude to a greater or lesser extent from the spring sleeve 30 via their free end through a feed-through channel. The spring elements 52 may be cut to length accordingly and possibly fixed to the spring sleeve 30, as has already been described above. The two spring elements 52 do not surround the bushing 16 or an electrical mating contact, but contact an electrical contact area of a mating contact on two diametrically opposed sides.

FIG. 11 shows a favorable embodiment of a spring sleeve 30 with three spring elements 52, which are offset by 120° around the bushing 16 and are inserted tangentially and substantially in elongate form through separate feed-through channels 20 into the spring sleeve 30.

FIG. 12 schematically illustrates a device 200 for producing a contact element 30. The device 200 comprises a transport mechanism 220 (only illustrated schematically) in order to transport a wire coil 50 via a guide element 212 to a spring sleeve 10, which is held ready in a working area of the device 200, and to insert said wire coil through a radial feed-through channel 20 in the wall of the spring sleeve 10 into a groove 18 in the spring sleeve 10. The device 200 further includes a cutting mechanism (not illustrated) in order to separate a spring element 52 (see FIG. 7) from the wire coil 50 and to cut said spring element to a desired length, and also a connection unit in order to fixedly connect, for example, to weld, the spring element 52 (see FIG. 7) to the spring sleeve 10 at least at one point. The cutting of the wire coil 50 and the fastening of the spring element 52 may advantageously be implemented by means of a laser, such that the cutting mechanism and the connection unit may also be identical.

The tangential feed-through channel 20 lies in the same plane as the groove, such that, as the wire coil 50 is transported, it can be inserted by its leading end through the tangential feed-through channel 20 in the wall of the spring sleeve 10 into the groove 18 within the spring sleeve 10 with a desired length, at most until the leading end in the groove 18 contacts a trailing area of the wire coil 50.

The inserted piece of the wire coil 50 can then be cut to a desired length, such that a spring element 52 (FIG. 7) remains in the spring sleeve 10. Before or after the cutting to length of the wire coil 50, the spring element 52 can be connected to the spring sleeve 10, in particular laser-welded at one point.

The wire coil 50 is then ready for charging the next provided spring sleeve 10 with a spring element 52 (see FIG. 7). A large number of spring elements 52 (see FIG. 7) can be formed from the wire coil 50 and are intended for insertion into prepared spring sleeves 10, such that a continuous automatic production process is possible from the winding of the wire coil 50 as far as and including the insertion of the spring elements 52 into the spring sleeves 10.

The wire coil 50 can be canted directly from a winding process via a canting stage 110, for example, two cylinders 210 rotating in opposite directions, between which the wire coil 50 is passed, and then transported by means of a schematically indicated transport arrangement 220 to the guide element 212.

The device 200 according to the present invention allows an automated economical method for producing a contact element 30 with spring element.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. An electrical contact element for a medical implant, comprising:
   a spring sleeve with a bushing for receiving an electrical mating contact in a direction of insertion;
   at least one groove that is arranged transversely around the bushing at least in areas and that is open to the bushing at least in areas;
   at least one spring element, arranged in the groove, for electrically contacting the electrical mating contact; and
   at least one feed-through channel for feeding the spring element into the at least one groove, which leads from an outer face of the spring sleeve to the at least one groove, wherein the at least one groove comprises a peripheral groove, and wherein the spring element is inserted so far into the peripheral groove in the spring sleeve that a leading free end of the spring element contacts a trailing area of the spring element.

2. The electrical contact element as claimed in claim 1, wherein the at least one feed-through channel extends transversely to the at least one groove.

3. The electrical contact element as claimed in claim 1, wherein the at least one feed-through channel extends tangentially to the at least one groove.

4. The electrical contact element as claimed in claim 3, wherein the spring element protrudes from the tangential feed-through channel.

5. The electrical contact element as claimed in claim 1, wherein the spring element is fixedly connected to the spring sleeve at least at one point.

6. The electrical contact element as claimed in claim 1, wherein the spring element finishes flush with the feed-through channel.

7. The electrical contact element as claimed in claim 1, wherein the spring sleeve is formed in two or more parts, and the groove lies in a parting plane.

8. The electrical contact element as claimed in claim 7, wherein the groove, when the two spring sleeve parts are joined together, has an undercut, such that, when the multi-part spring sleeve is assembled, the spring element is enclosed over more than half of its circumference by the groove.

9. The electrical contact element as claimed in claim 1, wherein the spring element is a wire coil.

10. A method for producing contact element as claimed in claim 1, wherein a wire coil is transported via a guide element into a feed-through channel of the spring sleeve and is inserted through the feed-through channel into the groove and is cut to a desired length.

11. The method as claimed in claim 10, wherein the wire coil is inserted so far into the groove until a leading free end of the spring element contacts a trailing area of the spring element.

12. The method as claimed in claim 10, wherein the wire coil is transported from a winding process via a canting stage to the guide element and is canted in the canting stage.

13. The method as claimed in claim 10, wherein the spring element is fixedly connected to the spring sleeve at least at one point.

* * * * *